United States Patent [19]

Challenger

[11] Patent Number: 5,166,406
[45] Date of Patent: Nov. 24, 1992

[54] PREPARATION OF GLUTARIC ACID DERIVATIVES

[75] Inventor: Stephen Challenger, Walmer, England

[73] Assignee: Pfizer Inc., New York, N.Y.

[21] Appl. No.: 504,493

[22] Filed: Apr. 4, 1990

[51] Int. Cl.$^5$ .............................................. C07C 69/74
[52] U.S. Cl. .................................................. 560/122
[58] Field of Search ......................... 560/122; 562/504

[56] References Cited

FOREIGN PATENT DOCUMENTS 274234 7/1988 European Pat. Off. .

OTHER PUBLICATIONS

Allinger, "Organic Chemistry," p. 524 (1971).
Payne, J. Org. Chem., 24 pp. 4793–4797 (1961).
Zavialov, Tetrahedron, 20 pp. 2745–2750 (1964).
Middeton, Aust. J. Chem., 33 pp. 2467–2476 (1980).
Mannich, Ber., 74, 1007 (1941).

Primary Examiner—Michael L. Shippen
Attorney, Agent, or Firm—Peter C. Richardson; Paul H. Ginsburg; Grover F. Fuller, Jr.

[57] ABSTRACT

The invention provides a process for preparing a compound of the formula:

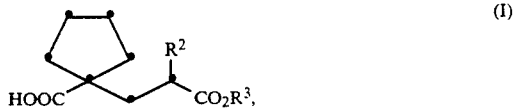

(I)

or a base salt thereof, wherein $R^2$ is hydrogen or $C_1$–$C_6$ alkyl optionally substituted by up to 3 substituents each independently selected from the group consisting of $C_1$–$C_6$ alkoxy and $C_1$–$C_6$ alkoxy($C_1$–$C_6$ alkoxy)-; and $R^3$ is $C_1$–$C_6$ alkyl or benzyl, said benzyl group being optionally ring-substituted by up to 2 nitro or $C_1$–$C_4$ alkoxy substituents comprising reacting a compound of the formula:

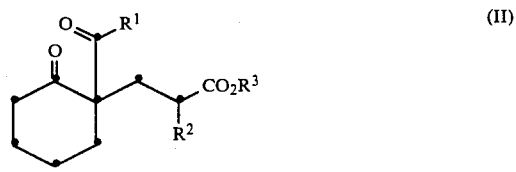

(II)

wherein $R^1$ is $C_1$–$C_4$ alkyl, phenyl or benzyl or $C_1$–$C_4$ alkoxy; and $R^2$ and $R^3$ are as previously defined for a compound of the formula (I), with hydrogen peroxide or a source of peroxide ions: said process being optionally followed by conversion of the compound of the formula (I) to a base salt thereof. The present invention also relates to novel compounds of the formula (II).

16 Claims, No Drawings

PREPARATION OF GLUTARIC ACID DERIVATIVES

FIELD OF THE INVENTION

This invention relates to a process for the preparation of glutaric acid derivatives.

BACKGROUND OF THE INVENTION

The invention relates to a process for the preparation of 1-[2-(alkoxycarbonyl)ethyl]-1-cyclopentanecarboxylic acid derivatives, the use of which has previously been disclosed in EP-A-0274334 as intermediates for the preparation of certain substituted glutaramide diuretic agents having utility in the treatment of hypertension, heart failure, renal insufficiency and in other disorders.

EP-A-0274234 describes two methods for the preparation of 1-[2-(alkoxycarbonyl)ethyl]-1-cyclopentanecarboxylic acid derivatives by which the dianion derived from cyclopentanecarboxylic acid by treatment with a strong base, e.g. lithium diisopropylamide, is treated with either (i) an acrylate derivative, or (ii) an ester of 3-bromopropanoic acid followed by optional further alkylation as required, to provide the desired products. However, the favored route, involving use of an acrylate derivative, can not be used for certain preferred embodiments of the present invention due to competing elimination reactions.

It has now been discovered that 1-[2-(alkoxycarbonyl)ethyl]-1-cyclopentanecarboxylic acid derivatives may be unexpectedly prepared by the oxidative rearrangement of 2-acyl- or 2-alkoxycarbonyl-cyclohexanone derivatives, offering further commercially important improvements over the existing processes such as ease and lower cost of operation.

SUMMARY OF THE INVENTION

The present invention provides a process for preparing a compound of the formula:

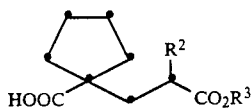
(I)

or a base salt thereof, wherein $R^2$ is hydrogen or $C_1-C_6$ alkyl optionally substituted by up to 3 substituents each independently selected from $C_1-C_6$ alkoxy and $C_1-C_6$ alkoxy ($C_1-C_6$ alkoxy)-; and $R^3$ is $C_1-C_6$ alkyl or benzyl, said benzyl group being optionally ring-substituted by up to 2 nitro or $C_1-C_4$ alkoxy substituents, comprising reacting a compound of the formula:

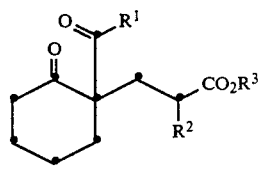
(II)

wherein $R^1$ is $C_1-C_4$ alkyl, phenyl, benzyl or $C_1-C_4$ alkoxy; and $R^2$ and $R^3$ are as previously defined for a compound of the formula (I), with hydrogen peroxide or a source of peroxide ions. The process can followed by conversion of the compound of the formula (I) to a base salt thereof.

Preferably, $R^1$ is $C_1-C_4$ alkyl, phenyl or $C_1-C_4$ alkoxy. More preferably, $R^1$ is methyl, phenyl or ethoxy. Most preferably, $R^1$ is methyl or ethoxy.

Preferably, $R^2$ is hydrogen or $C_1-C_6$ alkyl optionally substituted by one $C_1-C_6$ alkoxy or $C_1-C_6$ alkoxy ($C_1-C_6$ alkoxy)- substituent.

More preferably, $R^2$ is hydrogen, 2-methoxyethoxymethyl, 2-methoxyethyl or methoxymethyl.

Most preferably, $R^2$ is hydrogen or 2-methoxyethoxymethyl.

Preferably, $R^3$ is $C_1-C_6$ alkyl or benzyl, said benzyl group being optionally ring-substituted by one nitro or $C_1-C_4$ alkoxy substituent.

More preferably, $R^3$ is ethyl, tert-butyl, benzyl, 4-nitrobenzyl or 4-methoxybenzyl.

Most preferably, $R^3$ is tert-butyl.

Examples of base salts of the compounds of the formula (I) include alkali metal, alkaline earth metal, ammonium and mono-, di- or tri($C_1-C_4$ alkyl)ammonium salts.

Preferably the base salt of a compound of the formula (I) is the isopropylammonium salt.

The present invention also relates to novel compounds of the formula (II) which are useful as intermediates in the preparation of certain substituted glutaride diuretic agents having utility in the treatment of hypertension, heart failure, renal insufficiency, and in other disorders.

DETAILED DESCRIPTION OF THE INVENTION

The source of peroxide ions includes reagents such as hydrogen peroxide, peroxy acids (e.g. peroxy($C_1-C_4$)alkanoic acids), sodium perborate or a hydrate thereof, and sodium percarbonate, which are used in the presence of water. Preferably hydrogen peroxide, sodium perborate tetrahydrate or sodium percarbonate is used. Most preferably hydrogen peroxide is used.

The skilled man will appreciate that a certain amount of water must be present in the reaction mixture so that peroxide ions may be generated from the reagent.

The reaction is preferably carried out using hydrogen peroxide in the presence of water.

The reaction is preferably carried out in a suitable solvent in the presence of acid or base. Although the reaction does proceed slowly under neutral conditions, it has been found that acidic or basic reaction conditions accelerate the rate.

Suitable solvents for the reaction include $C_1-C_6$ alkanols and toluene.

Preferably the solvent is methanol, tert-butanol or toluene.

Most preferably the solvent is tert-butanol.

When the reaction is carried out in the presence of acid, preferred acids include mineral acids and $C_1-C_4$ alkanoic acids.

Preferably the acid is sulphuric acid or acetic acid. The reaction may also be carried out using a $C_1-C_4$ alkanoic acid as the solvent in the absence of an additional acid. Acetic acid is preferred.

When the reaction is carried out in the presence of base, preferred bases include sodium or potassium hydroxide, carbonate or bicarbonate.

Preferably the base is sodium hydroxide or sodium or potassium bicarbonate.

Sodium percarbonate is a basic reagent per se and is typically not used in the presence of acid or a further base.

The reaction conditions and, in particular, the solvent and the nature and/or concentration of the acid or base used in the process provided by the present invention are chosen such that the reaction proceeds safely and at a favorable rate, without hydrolysis or transesterification of the ester functionality in the starting material (II) or product (I) occurring.

A preferred embodiment of the present invention provides a process for preparing a compound of the formula (I), or a base salt thereof, comprising reaction of a compound of the formula (II) with
(a) aqueous hydrogen peroxide in
  (i) a suitable organic solvent in the presence of an acid,
  (ii) a suitable organic solvent in the presence of a base, or
  (iii) a $C_1$-$C_4$ alkanoic acid;
(b) sodium perborate, or a hydrate thereof, in a $C_1$-$C_4$ alkanoic acid; or
(c) sodium percarbonate in a suitable organic solvent in the presence of water: said process being optionally followed by a conversion of the compound of the formula (I) to a base salt thereof,
wherein $R^1$, $R^2$ and $R^3$ are as previously defined for compounds of the formulae (I) and (II).

A most preferred embodiment of the present invention provides a process for preparing a compound of the formula (I), or a base salt thereof, comprising reaction of a compound of the formula (II) with
(a) aqueous hydrogen peroxide in
  (i) tert-butanol or toluene in the presence of a catalytic amount of sulphuric acid,
  (ii) either tert-butanol in the presence of sodium or potassium bicarbonate, or methanol in the presence of sodium hydroxide, or
  (iii) acetic acid;
(b) sodium perborate tetrahydrate in acetic acid; or
(c) sodium percarbonate in tert-butanol in the presence of water: said process being optionally followed by conversion of the compound of the formula (I) to a base salt thereof, wherein $R^1$, $R^2$ and $R^3$ are as previously defined for compounds of the formulae (I) and (II).

Sodium perborate is commercially available in several different hydrate forms, although the tetrahydrate (e.g. available from the Aldrich Chemical Company Ltd.) is preferred for the purpose of the present invention. Sodium perborate tetrahydrate may be formulated as either $NaBO_3.4H_2O$ or $NaBO_2.H_2O_2.3H_2O$ and provides a source of peroxide ions in aqueous solution:

$$[B(OH)_3(O_2H)]^- + H_2O \rightarrow [B(OH)_4]^- + H_2O_2$$

(see F. A. Cotton and G. Wilkinson, Advanced Inorganic Chemistry, 5th Edition, page 172).

Sodium percarbonate is a commercially available (e.g. from Fluka Chemicals Ltd.) bleaching agent and provides a source of peroxide ions in the presence of water. The molecular formula is generally represented as $Na_2CO_3.3/2\ H_2O_2$ (see Chem. Lett., 1986, 665-6).

Alkyl and alkoxy groups containing 3 or more carbon atoms and $C_4$-alkanoic acids may be straight or branched chain.

The process provided by the present invention may be carried out according to the following methods:

1. In a typical procedure, a stirred solution of a compound of the formula (II) in a suitable organic solvent, e.g. t-butanol or toluene, is cautiously treated with an aqueous (typically about 30 weight %) solution of hydrogen peroxide and a catalytic amount of a suitable acid, e.g. sulphuric acid, preferably maintaining the reaction temperature at below 50° C., most preferably at about room temperature, throughout the addition. The reaction is further stirred at room temperature for up to 24 hours although longer reaction times may be necessary. The product of the formula (I) is isolated and purified using conventional techniques.

2. In a typical procedure, a stirred solution of compound of the formula (II) in a suitable organic solvent, e.g. $C_1$-$C_4$ alkanol such as tert-butanol or methanol, is cautiously treated with a suitable base, e.g. sodium or potassium hydroxide or bicarbonate, and an aqueous (typically about 30 weight %) solution of hydrogen peroxide, maintaining the reaction temperature at from 0° C. to 50° C. throughout the additions. The reaction is further stirred at from room temperature to 50° C. for up to 24 hours, or longer if necessary. The product of the formula (I) is isolated and purified by conventional techniques.

3. In a typical procedure, a stirred solution of a compound of the formula (II) in a $C_1$-$C_4$ alkanoic acid, e.g. acetic acid, is cautiously treated with an aqueous (typically about 30 weight %) solution of hydrogen peroxide, maintaining the reaction temperature at below 40° C. throughout the addition to avoid hydrolysis of the ester functionalility. The reaction is further stirred at room temperature for up to 24 hours. The product of the formula (I) is isolated and purified using conventional techniques.

4. In a typical procedure, a stirred solution of a compound of the formula (II) in a $C_1$-$C_4$ alkanoic acid, e.g. acetic acid, is treated portionwise with sodium perborate tetrahydrate maintaining the reaction temperature at below 20° C. during the addition. The mixture is further stirred at room temperature for up to 48 hours. The product of the formula (I) is isolated and purified using conventional techniques.

5. In a typical procedure, a stirred solution of a compound of the formula (II) in a suitable organic solvent, e.g. a $C_1$-$C_4$ alkanol such as tert-butanol, is treated with sodium percarbonate at about room temperature. The reaction is stirred at from room temperature to 60° C. for about 24 hours. The product of the formula (I) is isolated and purified by conventional techniques.

It will be appreciated by the skilled man that the reaction time will vary in each individual case dependent on several factors, such as the nature of the substituents and the reaction temperature employed.

The course of the reaction may be monitored using conventional methods, e.g. thin-layer chromatography.

The starting materials of the formula (II) may be prepared by a Michael addition reaction as illustrated in Scheme 1, using comparable reaction conditions to those described by Kryshtal et al, Synthesis, [1979], 107.

Scheme 1

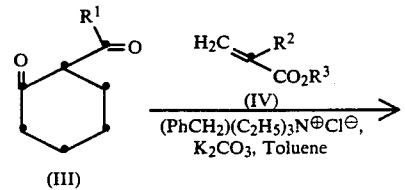

-continued
Scheme 1

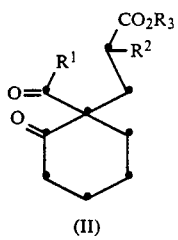

(II)

wherein $R^1$, $R^2$ and $R^3$ are as previously defined for a compound of the formula (I).

In a typical procedure, an acrylate derivative of the formula (IV) is added to a stirred mixture of a compound of the formula (III), potassium carbonate and a catalytic amount of benzyltriethylammonium chloride in toluene at about room temperature, and the reaction further stirred at from room temperature to 50° C., preferably at about 40° C., for up to 24 hours. The product of the formula (II) is isolated and purified using conventional techniques.

The reaction may also be performed in the absence of benzyltriethylammonium chloride by reacting a compound of the formula (III) with an acrylate derivative of the formula (IV) in the presence of a suitable base, e.g. potassium carbonate or potassium tert-botoxide, in a suitable organic solvent, e.g. a $C_1$–$C_4$ tert-butanol) or acetonitrile, at about room temperature. When $R^2$ is other than hydrogen in this reaction and potassium tert-butoxide is used as the base, it is preferably added to the reaction mixture at about $-10°$ C. and this is followed by a period of stirring of the reaction at from 0° C. to room temperature. The product of the formula (II) is isolated and purified by conventional techniques.

The compounds of the formula (III) and the acrylate derivatives of the formula (IV) are either known compounds which may also be commercially available, or are prepared by conventional methods in accordance with literature precedents.

A base salt of a compound of the formula (I) may be prepared by mixing together solutions containing approximately equimolar amounts of a compound of the formula (I) and a suitable base. The base salt is recovered by filtration or by filtration or by evaporation of the solvent.

The process provided by the invention is illustrated by the following Examples:

EXAMPLE 1

[2-(tert-Butoxycarbonyl)ethyl]-1-cyclopentanecarboxylic acid

To a solution of crude 2-acetyl-2-[2-(tert-butoxycarbonyl)-ethyl]cyclohexanone (see Preparations 1 and 2) (42 g, 0.15 mol) in t-butanol (84 ml) was cautiously added a 30% aqueous hydrogen peroxide solution (21 ml, 0.187 mol) and conc. sulphuric acid (0.25 ml, 98% w/w) at room temperature, maintaining the reaction temperature below 50° C. during the addition. The mixture was stirred at room temperature for 18 hours, partitioned between dichloromethane (100 ml) and water (100 ml), and the layers separated. The dichloromethane layer was washed with 5% aqueous sodium sulphite solution (50 ml), dried over magnesium sulphate, filtered and concentrated under reduced pressure to give a pale yellow solid, (43 g). The solid partially crystallized on standing overnight to provide, after collecting and washing with pentane, the title compound, (15.5 g).

The mother liquors were concentrated and purified by column chromatography on silica gel by eluting with ethyl acetate/hexane (1:10) to provide, after combination and evaporation of appropriate fractions, a further 14.47 g of the title compound (combined yield 29.97 g, 78%).

$^1$H-NMR (300 MHz, CDCl$_3$): =1.45 (s, 9H), 1.45–1.60 (m, 2H), 1.62–1.78 (m, 4H), 1.92–1.99 (m, 2H), 2.11–2.21 (m, 2H), 2.21–2.33 (m, 2H) ppm.

EXAMPLE 2

1-[2-(tert-Butoxycarbonyl)ethyl]-1-cyclopentanecarboxylic acid

To a solution of 2-acetyl-2-[2-(tert-butoxycarbonyl)ethyl]-cyclohexanone (see Preparations 1 and 2) (2.0 g, 7.45 mmol) and concentrated sulphuric acid (98% w/w, one drop) in toluene (6.0 ml) was added, dropwise, a 30% aqueous solution of hydrogen peroxide (1.05 ml, 9.31 mmol) at room temperature. The mixture was stirred for 68 hours at room temperature, treated with a further quantity of a 30% aqueous solution of hydrogen peroxide (0.4 ml, 3.72 mmol) and stirred for a further 16 hours at room temperature. The mixture was partitioned between toluene (25 ml) and 5% aqueous sodium sulphite solution and the layers separated. The toluene layer was washed with dilute aqueous ammonia solution (25 ml of 0.880 ammonia in 200 ml of distilled water, 4×25 ml). The combined aqueous extracts were washed with toluene (25 ml), acidified to pH 2-3 with 5.0N aqueous hydrochloric acid solution and extracted with toluene (3×25 ml). The combined toluene extracts were dried over magnesium sulphate, filtered and concentrated under reduced pressure to give an oil, (1.11 g, 61%). The crude product was crystallized from pentane (7.5 ml/g) to give the title compound as a colorless solid. Rf. 0.28 (silica, hexane/ethyl acetate 2:1).

$^1$H-NMR (300 MHz, CDCl$_3$) =1.45 (s, 9H). 1.45–1.60 (m, 2H), 1.62–1.78 (m, 4H), 1.92–1.99 (m, 2H), 2.11–2.21 (m, 2H), 2.21–2.33 (m, 2H) ppm. Analysis %: Found: C, 64.26; H, 9.27; $C_{13}H_{22}O_4$ requires C, 64.44; H, 9.15.

EXAMPLE 3

1-[2-Benzyloxycarbonyl)ethyl]-1-cyclopentanecarboxylic acid

To a solution of crude 2-acetyl-2-[2-(benzyloxycarbonyl)-ethyl]cyclohexanone (see Preparation 3) (19.7 g, 0.065 mol) in tert-butanol (35 ml) at room temperature was cautiously added, over a period of 30 minutes, a 30% aqueous hydrogen peroxide solution (8.8 ml, 0.078 mol) and concentrated sulphuric acid (0.25 ml, 98% w/w). The mixture was stirred at room temperature for 20 hours, partitioned between dichloromethane (100 ml) and water (100 ml) and the layers separated. The dichloromethane layer was washed with a 5% aqueous sodium sulphite solution (50 ml), dried over magnesium sulphate, filtered and concentrated under reduced pressure. Purification of the residue by chromatography on silica gel by initially eluting with ethyl acetate/hexane (1:2 changing to 1:1), followed by neat ethyl acetate in the latter stages, gave, after combination and evaporation of appropriate fractions, the title compound as a yellow oil, (12.17 g, 72%). RF. 0.17 (silica, hexane/ethyl acetate/acetic acid, 74:25:1). IR (thin film): $v$=3800–2400, 1735, 1695, 1450 cm$^{-1}$. Analysis %:

Found: C, 69.70; H, 7.18; C$_{16}$H$_{20}$O$_4$ requires: C, 69.55; H, 7.29.

EXAMPLE 4

1-[2-(Ethoxycarbonyl)ethyl]-1-cyclopentanecarboxylic acid

To a solution of 2-acetyl-2-[2-(ethoxycarbonyl)ethyl]-cyclohexanone (see Preparation 4) (40 g, 0.16 mol) in tert-butanol (85 ml) was added, dropwise, a 30% aqueous solution of hydrogen peroxide (21.7 ml, 0.19 mol) and concentrated sulfuric acid (0.25 ml, 98% w/w) at room temperature. The mixture was further stirred for 24 hours, partitioned between dichloromethane (100 ml) and distilled water (100 ml) and the layers separated. The dichloromethane layer was washed with 5% aqueous sodium sulphite solution, dried over magnesium sulphate, filtered and concentrated under reduced pressure to give a yellow oil, (34.35 g). Purification of this material by chromatography on silica by eluting with ethyl acetate/hexane (1:2 changing to 1:1), followed by neat ethyl acetate in the latter stages, gave, after combination and evaporation of appropriate fractions, the title compound as a yellow oil, (22.96 g, 67%). RF. 0.28 (silica, ethyl acetate/hexane, 1:1). $^1$H-NMR (300 MHz, CDCl$_3$): =1.31 (t, 3H), 1.47–1.62 (m, 2H), 1.62–1.82 (m, 4H), 1.92–2.08 (m, 2H), 2.10–2.27 (m, 2H), 2.32–2.46 (m, 2H), 4.19 (q, 2H) ppm. $^{13}$C-NMR (75.5 MHz, CDCl$_3$) 14.26, 25.15, 31.21, 33.56, 36.15, 53.21, 60.49, 173.38, 183.52 ppm.

EXAMPLE 5

1-[2-(tert-Butoxycarbonyl)-3-(2-methoxyethoxy)-propyl]-1-cyclopentanecarboxylic acid To a solution of 2-acetyl-2-[2-(tert-butoxycarbonyl)-3-(2-methoxyethoxy)propyl]cyclohexanone (see Preparations 5 and 11) (50 m9, 0.14 mmol) in tert-butanol (0.5 ml) was added a 30% aqueous hydrogen peroxide solution (0.02 ml, 0.168 mmol) and concentrated sulphuric acid (one drop) at room temperature. The mixture was stirred at room temperature for 4 hours, partitioned between dichloromethane (10 ml) and water (10 ml), and the layers separated. The aqueous layer was extracted with dichloromethane (2×10 ml), the combined organic extracts dried over magnesium sulphate, filtered and concentrated under reduced pressure to give the title compound, (49 mg). Rf. 0.36 (silica, ethyl acetate). $^1$H-NMR (300 MHz, CDCl$_3$) =1.43 (s, 9H), 1.43–1.60 (m, 2H), 1.61–1.65 (m, 4H), 1.78 (dd, 1H), 2.0 (dd, 1H), 2.08–2.20 (m, 2H), 2.59–2.70 (m, 1H), 3.38 (s, 3H), 3.48–3.65 (m, 6H) ppm.

EXAMPLE 6

1-[2-(tert-Butoxycarbonyl)-3-(2-methoxyethoxy)-propyl]-1-cyclopentanecarboxylic acid isopropylamine salt (1:1)

To a solution of 2-acetyl-2-[2-tert-butoxycarbonyl)-3-(2-methoxyethoxy)propyl]cyclohexanone (see Preparations 5 and 11)) (5.45 g, 0.015 mol) in tert-butanol (10.9 ml) and concentrated sulphuric acid (one drop) was added a 30% aqueous hydrogen peroxide solution (2.1 ml, 0.018 mol) at room temperature. The mixture was stirred at room temperature for 24 hours, partitioned between dichloromethane (20 ml) and 2.0M aqueous sodium hydroxide solution (20 ml) and the layers separated. The dichloromethane layer was washed with water (10 ml), the combined aqueous extracts acidified to pH 2 with 5.0M aqueous hydrochloric acid solution and extracted with n-hexane (2×20 ml). The combined n-hexane extracts were washed with water (5 ml), concentrated under reduced pressure and azeotropically dried with ethyl acetate to give the title acid, (3.99 g, 96% by GC normalization). Rf. 0.44 (silica, ethyl acetate, 1% acetic acid). $^{13}$C-NMR (75.5 MHz, CDCl$_3$) =24.44, 24.80, 27.82, 34.97, 36.51, 37.29, 44.43, 53.35, 58.84, 70.06, 71.72, 73.20, 80.44, 173.88, 183.33 ppm.

The crude product (3.4 g, 0.01 mol) was dissolved in 34 ml of n-hexane and isopropylamine (0.61 g, 0.01 mol) added at room temperature. The precipitated salt was cooled to 0° C., granulated for 2 hours and collected to give the title compound (3.57 g, 72.1% overall yield; HPLC main band assay 98.7%), m.p. 84°–87° C. $^1$H-NMR (300 MHz, CDCl$_3$): =1.23 (d, 6H), 1.45 (s, 9H), 1.35–1.50 (m, 2H), 1.58–1.70 (m, 4H), 1.78 (dd, 1H), 1.88 (dd, 1H), 2.05–2.19 (m, 2H), 2.60–2.69 (m, 1H), 3.28 (heptet, 1H), 3.36 (s, 3H), 3.48–3.62 (m, 6H), 5.98 (brs, 3H) ppm. $^{13}$C-NMR (75 MHz, CDCl$_3$) =21.99, 24.51, 24.97, 27.86, 34.64, 37.14, 37.98, 43.05, 44.94, 54.57, 58.78, 69.91, 71.68, 73.48, 79.98, 174.79, 183.22 ppm. Analysis %: Found: C, 61.64; H, 10.30; N, 3.46; C$_{20}$H$_{39}$NO$_6$ requires: C, 61.67; H, 10.09; N, 3.60.

EXAMPLE 7

1-[2-(4-Nitrobenzyloxycarbonyl)ethyl]-1-cyclopentanecarboxylic acid

To a solution of 2-acetyl-2-[2-(4-nitrobenzyloxycarbonyl)-ethyl]cyclohexanone (see Preparation 8) (1.68 g, 4.85 mmol) in tert-butanol (3.3 ml) was added, dropwise, a 30% aqueous solution of hydrogen peroxide (0.65 ml, 5.82 mmol) and concentrated sulphuric acid (98% w/w, one drop) at room temperature. The mixture was stirred for 48 hours, partitioned between toluene (25 ml) and 5% aqueous sodium sulphite solution and the layers separated. The toluene layer was washed with dilute aqueous ammonia solution (25 ml of 0.880 ammonia in 200 ml of distilled water, 4×25 ml). The combined aqueous extracts were washed with toluene (25 ml), acidified to pH 2–3 with 5.0N aqueous hydrochloric acid solution and extracted with toluene (3×25 ml). The combined toluene extracts were dried over magnesium sulphate, filtered and concentrated under reduced pressure to give an oil which solidified on standing, (0.96 g, 61.9%). The crude product was recrystallized from ethyl acetate/hexane 1:1 (3 ml/g) to give the title acid, m.p. 78°–80° C. Rf. 0.27 (silica, hexane/ethyl acetate 2:1 +1% acetic acid). $^1$H-NMR (300 MHz, CDCl$_3$) 1.49–1.61 (m, 2H), 1.63–1.78 (m, 4H), 1.97–2.06 (m, 2H), 2.11–2.22 (m, 2H), 2.42–2.50 (m, 2H), 5.22 (s, 2H), 7.55 (d, 2H), 8.23 (d, 2H) ppm. $^{13}$C-NMR (75 MHz, CDCl$_3$): 24.98, 30.80, 33.12, 36.03, 52.86, 64.71, 123.68, 128.30, 143.03, 147.61, 172.71, 183.79 ppm. Analysis %: Found: C, 59.71; H, 5.86; N, 4.44; C$_{16}$H$_{19}$NO$_6$ requires C, 59.81; H, 5.96; N, 4.36.

EXAMPLE 8

1-[2-(4-Methoxybenzyloxycarbonyl)ethyl]1-cyclopentanecarboxylic acid

To a solution of 2-benzoyl-2-[2-(4-methoxybenzyloxycarbonyl)-ethyl]cyclohexanone (see Preparation 9) (2.16 g, 5.47 mmol) in tert-butanol (4.3 ml) was added, dropwise, a 30% aqueous solution of hydrogen peroxide (0.74 ml, 6.56 mmol) and concentrated sulphuric acid (98% w/w, one drop) at room temperature. The mixture was stirred for 48 hours, partitioned between toluene (25 ml) and 5% aqueous sodium sulphite solution and the layers separated. The toluene layer was washed with dilute aqueous ammonia solution (25 ml of 0.880 ammonia in 200 ml of distilled water, 4×25 ml). The combined aqueous extracts were washed with toluene (25 ml), acidified to pH 2-3 with 5.0N aqueous hydrochloric acid solution and extracted with toluene (3×25 ml). The combined toluene extracts were dried over magnesium sulphate, filtered and concentrated under reduced pressure to give the title compound as an oil, (0.746 g, 44.6%). R.F. 0.16 silica, hexane/ethyl acetate 2:1). $^1$H-NMR (300 MHz, CDCl$_3$) =1.45-1.59 (m, 2H), 1.65-1.78 (m, 4H), 1.98-2.06 (m, 2H), 2.12-2.22 (m, 2H), 2.34-2.46 (m, 2H), 3.84 (s, 3H), 5.06 (s, 2H), 6.91 (d, 2H), 7.31 (d, 2H) ppm. Analysis %: Found: C, 67.05; H, 7.18; C17 H2205 requires C, 66.65; H, 7.24.

EXAMPLE 9

1-[2-(tert-Butoxycarbonyl)ethyl]-1-cyclopentanecarboxylic acid

To a solution of 2-acetyl-2-[2-(tert-butoxycarbonyl)ethyl]cyclohexanone (see Preparations 1 and 2) (2.06 g, 7.67 mmol) in methanol (8.0 ml) was added, dropwise, a 30% aqueous solution of hydrogen peroxide (1.04 ml, 9.21 mmol) at room temperature. The mixture was cooled to 0° C. and a 20% aqueous solution of sodium hydroxide (1.0 ml) added dropwise. The mixture was stirred for 24 hours at room temperature, partitioned between toluene (25 ml) and 5% aqueous sodium sulphite solution and the layers separated. The toluene layer was washed with dilute aqueous ammonia solution (25 ml of 0.880 ammonia in 200 ml of distilled water, 4×25 ml). The combined aqueous extracts were acidified to pH 2-3 with 5.0N aqueous hydrochloric acid solution and extracted with toluene (3×25 ml). The combined toluene extracts were dried over magnesium sulphate, filtered and concentrated under reduced pressure to give the title acid as a colorless oil, (0.816 g, 44%). R.f. 0.24 (silica, hexane/ethyl acetate 2:1). $^1$H-NMR (300 MHz, CDCl$_3$) =1.45 (s, 9H), 1.45-1.60 (m, 2H), 1.62-1.78 (m,4H), 1.92-1.99 (m, 2H), 2.11-2.21 (m, 2H), 2.21-2.33 (m, 2H) ppm.

EXAMPLE 10

1-[2-(tert-Butoxycarbonyl)ethyl]-1-cyclopentanecarboxylic acid

To a solution of 2-acetyl-2-[2-(tert-butoxycarbonyl)ethyl]cyclohexanone (see Preparations 1 and 2) (2.0 g, 7.45 mmol) in tert-butanol (4.0 ml) was added, in one portion, sodium percarbonate (0.935 g, 5.96 mmol) at room temperature. The mixture was heated to 50°-55° C. for 8 hours, stirred at room temperature for 16 hours, partitioned between toluene (25 ml) and 5% aqueous sodium sulphite solution and the layers separated. The toluene layer was washed with dilute aqueous ammonia solution (25 ml of 0.880 ammonia in 200 ml of distilled water, 4×25 ml). The combined aqueous extracts were acidified to pH 2-3 with 5.0N aqueous hydrochloric acid solution and extracted with toluene (3×25 ml). The combined toluene extracts were dried over magnesium sulphate, filtered and concentrated under reduced pressure to give the title acid as a colorless oil which solidified on standing, (1.119 g, 62%). R.f. 0.25 (silica, hexane/ethyl acetate 2:1). $^1$H-NMR (300 MHz, CDCl$_3$): 1.45 (s, 9H), 1.45-1.60 (m, 2H), 162-1.78 (m, 4H), 1.92-1.99 (m, 2H), 2.11-2.21 (m, 2H), 2.21-2.33 (m, 2H) ppm.

EXAMPLE 11

1-[2-(tert-Butoxycarbonyl)ethyl]-1-cyclopentanecarboxylic acid

To a solution of 2-acetyl-2-[2-(tert-butoxycarbonyl)ethyl]cyclohexanone (see Preparations 1 and 2) (1.0 g, 3.72 mmol) in acetic acid (10 ml) was added sodium perborate tetrahydrate (0.57 g, 3.72 mmol) in one portion at 15° C. The mixture was mechanically stirred for 1 hour during which time the internal temperature rose to 18° C. A further portion of sodium perborate tetrahydrate (0.57 g, 3.72 mmol) was then added and the mixture stirred for a further 1 hour. After this time a final portion of sodium perborate tetrahydrate (0.57 g, 3.72 mmol) was added and the mixture stirred at room temperature for 48 hours. The reaction was filtered to remove solids and the filter pad washed with ethyl acetate (2×25 ml). The combined filtrate and washings were washed with 5% aqueous sodium sulphite solution (2×50 ml), dried over magnesium sulphate, filtered and concentrated under reduced pressure to give a colourless oil, (0.92 g). The crude product was crystallized from pentane (4 ml/g) to give the title acid as a colorless solid, (0.617 g, 68.5%). R.f. 0.3 (silica, hexane/ethyl acetate, 2:1). $^1$H-NMR (300 MHz, CDCl$_3$) 1.45 (s, 9H), 1.45-1.60 (m, 2H), 1.62-1.78 (m, 4H), 1.92-1.99 (m, 2H), 2.11-2.21 (m, 2H), 2.21-2.33 (m, 2H) ppm. Analysis %: Found: C, 64,32; H, 9.03; C$_{13}$H$_{22}$O$_4$ requires: C, 64.44; H, 9.15.

EXAMPLE 12

1-[2-(tert-Butoxycarbonyl)ethyl]-1-cyclopentanecarboxylic acid

To a suspension of 2-[2-(tert-butoxycarbonyl)ethyl]-2-ethoxycarbonylcyclohexanone (see Preparation 10) (1.0 g, 3.35 mmol) and sodium hydrogen carbonate (0.281 g, 3.35 mmol) in tert-butanol (2.0 ml) was added, in four portions over a period of 1.5 hours, a 30% aqueous solution of hydrogen peroxide (4×0.11 ml, 4.0 mmol) at 40° C. The mixture was stirred at 40° C. for 20 hours. A fifth charge of a 30% aqueous solution of hydrogen peroxide (0.11 ml) and a further quantity of sodium hydrogen carbonate (0.281 g, 33.5 mmol) was added, and the mixture stirred at 40° C. for 8 hours. The mixture was partitioned between hexane (40 ml) and 5% aqueous sodium sulphite solution (25 ml) and the layers separated. The hexane layer was washed with dilute aqueous ammonia solution (25 ml of 0.880 ammonia in 200 ml of distilled water, 5×40 ml). The combined aqueous extracts were acidified to pH 2-3 with 5.0N aqueous hydrochloric acid solution and extracted with dichloromethane (3×25 ml). The combined dichloromethane extracts were washed with distilled water (25 ml), dried over magnesium sulphate, filtered and concentrated under reduced pressure to give the title compound as an oil, (0.362 g, 44.6%). R.f. 0.29 (silica, hexane/ethyl acetate 2:1). Analysis %: Found: C, 64.78; H, 9.39; C$_1$H$_{22}$O$_4$ requires: C, 64.44; H, 9.15.

The following Preparations illustrates the preparation of certain intermediates used in the preceeding Examples:

PREPARATION 1

2-Acetyl-2-[2-(tert-butoxycarbonyl)ethyl]cyclohexanone

To a suspension of 2-acetylcyclohexanone (100 g, 0.71 mol), potassium carbonate (118.3 g, 0.85 mol) and benzyltriethylammonium chloride (3.18 g, 0.014 mol) in toluene (280 ml), was added, in one portion, tert-butyl acrylate (137.1 g, 155.2 ml, 1.07 mol) at room temperature. The suspension was stirred at 40° C. for 18 hours, diluted with distilled water (1 L) and toluene (500 ml), and the layers separated. The aqueous layer was extracted with toluene (3×500 ml), the combined toluene extracts dried over magnesium sulphate, filtered and concentrated under reduced pressure to give a brown oil, (197.8 g) Rf. 0.41 (silica, hexane/ethyl acetate, 3:1). The crude product was used without further purification.

An analytical sample was prepared from the crude reaction product by chromatography on silica gel by eluting with ethyl acetate/hexane (1:4) to provide, after combination and evaporation of appropriate fractions, the title compound as a colorless oil. IR (thin film): $v=2980, 2940, 2870, 1725, 1695, 1500, 1365 cm^1$. Analysis %: Found: C, 67.22; H, 8.64; $C_{15}H_{24}O_4$ requires C, 67.14; H, 9.01.

PREPARATION 2

2-Acetyl-2-[2-(tert-butoxycarbonyl)ethyl]cyclohexanone

To a suspension of 2-acetylcyclohexanone (2.8 g, 0.02 mol) and potassium carbonate (2.8 g, 0.02 mol) in tert-butanol (16.8 ml) was added tert-butyl acrylate (3.33 g, 0.026 mol) over a period of 10 minutes at room temperature. The suspension was stirred at room temperature for 48 hours, diluted with distilled water (16.8 ml) and dichloromethane (16.8 ml) and the layers separated. The aqueous layer was extracted with dichloromethane (16.8 ml) and the combined dichloromethane extracts concentrated under reduced pressure to give a brown oil (5.05 g). The crude product was crystallized from n-pentane (50 ml) to give the title compound as a colorless solid, (3.02 g, 56.2%), m.p. 47°–53° C. Rf. 0.41 (silica, hexane/ethyl acetate 2:1). $^1$H-NMR (300 MHz, $CDCl_3$): =1.41–1.55 (m, 2H), 1.47 (s, 9H), 1.62–1.84 (m, 4H), 1.96–2.04 (m, 2H), 2.10–2.21 (m, 2H), 2.17 (s, 3H), 2.26–2.53 (m, 2H) ppm. Analysis %: Found: C, 66.89; H, 9.04; $C_{15}H_{24}O_4$ requires C, 67.14; H, 9.01.

PREPARATION 3

2-Acetyl-2-[2-(benzyloxycarbonyl)ethyl]cyclohexanone

To a solution of 2-acetylcyclohexanone (9.6 g, 0.068 mol), potassium carbonate (11.3 g, 0.082 mol) and benzyltriethylammonium chloride (0.3 g, 0.0013 mol) in toluene (26 ml), was added benzyl acrylate (16.72 g, 0.103 mol) at room temperature. The mixture was heated at 40° C. for 20 hours, cooled, partitioned between water (200 ml) and toluene (200 ml) and toluene (200 ml) and the layers separated. The aqueous layer was extracted with toluene (2×200 ml), the combined organic extracts dried over magnesium sulphate, filtered and concentrated under reduced pressure to provide the title compound as a pale yellow oil, (20.7 g), Rf. 0.2 (silica, hexane/diethyl ether, 2:1). The crude product was used without further purification.

An analytical sample was prepared from the crude reaction product by chromatography on silica gel by eluting with hexane/ether (2:1) to provide, after combination and evaporation of appropriate fractions, the product as a colorless oil. IR (thin film): $v = 2940, 2870, 1735, 1715, 1695, 1450 cm^{-1}$. Analysis %: Found: C, 71.57; H, 7.45; $C_{18}H_{22}O_4$ requires: C, 71.50; H, 7.33%.

PREPARATION 4

2-Acetyl-2-[2-(ethoxycarbonyl)ethyl]cyclohexanone

To a solution of 2-acetylcyclohexanone (25 g, 0.18 mol), potassium carbonate (29.5 g, 0.21 mol) and benzyltriethylammonium chloride (0.8 g, 0.0035 mol) in toluene (70 ml) was added ethyl acrylate (29 ml, 27 g, 0.27 mol) at room temperature. The mixture was heated at 40° C. for 20 hours, filtered and partitioned between distilled water (200 ml) and toluene (200 ml). The organic layer was dried over magnesium sulphate, filtered and concentrated under reduced pressure to give the title compound as a brown oil, (41.7 g, 97%).

The crude product was used in Example 4 without further purification.

PREPARATION 5

2-Acetyl-2-[2-tert-butoxycarbonyl)-3-(2-methoxyethoxy)propyl]cyclohexanone

To a suspension of 2-acetylcyclohexanone (103 mg, 0.88 mmol), potassium carbonate (121 mg, 0.88 mmol) and benzyltriethylammonium chloride (3 mg, 0.015 mmol) in toluene (0.5 ml) was added, in one portion, tert-butyl 2-(2-methoxyethoxymethyl)acrylate (see Preparations 6 and 7) (191 mg, 0.88 mmol) at room temperature. The suspension was stirred at room temperature for 18 hours, at 40° C. for 8 hours, colled and diluted with water (10 ml) and extracted with ethyl acetate (3×10 ml). The combined organic extracts were dried over magnesium sulphate and concentrated to dryness under reduced pressure. The crude product was purified by flash column chromatography on silica gel by eluting with hexane/ethyl acetate (2:1) to provide, after combination and evaporation of appropriate fractions, the desired product as a colorless oil, (86 mg). Rf. 0.2 (silica, hexane/ethyl acetate, 2:1). IR (thin film: $v=2980, 2935, 2870, 1720, 1695, 1450 cm^{-1}$. Analysis %: Found: C, 64.22; H, 9.03; $C_{19}H_{32}O_6$ requires: C, 64.02; H, 9.03.

PREPARATION 6 tert-Butyl 2-(2-methoxyethoxymethyl)acrylate

To a solution of tert-butyl 2-(bromomethyl)acrylate (2.0 g, 9.0 mmol) in 2-methoxyethanol (30 ml) at 0° C. was added, in one portion, potassium carbonate (2.5 g, 18 mmol) and the mixture stirred at 0° C. for 1 hour. The reaction was diluted with distilled water (100 ml) and extracted with dichloromethane (100 ml). The layers were separated and the aqueous layer further extracted with dichloromethane (2×50 ml). The combined organic extracts were dried over magnesium sulphate, filtered and concentrated under reduced pressure. The residue was purified by chromatography on silica by eluting with hexane/ethyl acetate (2:1) to give, after combination and evaporation of appropriate fractions, the title compound as a yellow oil, (1.6 g, 82%). Rf. 0.32 (silica, hexane/ethyl acetate, 2:1). $^1$H-NMR (300 MHz, $CDCl_3$) 1.50 (s, 9H), 3.42 (s, 3H), 3.56–3.63

(m, 2H), 3.65-3.74 (m, 2H), 4.25 (s, 2H), 5.84 (s, 1 H), 6.25 (s, 1H) ppm.

PREPARATION 7 tert-Butyl 2-(2-methoxyethoxymethyl)acrylate a. tert-Butyl 2-(4-methylphenylsulphonylmethyl)acrylate To a solution of tert-butyl methacrylate (10 g, 70.3 mmol) in dichloromethane (44 ml) was added, in one portion, p-toluenesulphinic acid, sodium salt, dihydrate (15 g, 70.3 mmol) followed by iodine (17.8 g, 70.3 mmol) and the mixture stirred at room temperature for 24 hours. The reaction was cooled to 0° C. and triethylamine (10.6 g, 105.4 mmol) was added over a period of 10 minutes. The mixture was stirred at 0° C. for 15 minutes and at room temperature for 3 hours, diluted with dichloromethane (100 ml) and distilled water (100 ml). The layers were separated and the aqueous layer further extracted with dichloromethane (50 ml). The combined organic extracts were washed with 1.0N aqueous hydrochloric acid solution (50 ml), saturated aqueous sodium hydrogen carbonate solution (50 ml), distilled water (50 ml) and concentrated under reduced pressure to give a yellow-brown oil, (19.63 g). The material was dissolved in ethyl acetate (40 ml) and triethylamine (7.1 g, 70.3 mmol) added. The mixture was heated at reflux for 8 hours and stirred at room temperature for 16 hours, washed with distilled water (100 ml), 1.0N aqueous hydrochloric acid solution (100 ml), saturated aqueous sodium hydrogen carbonate solution (100 ml) and the organic layer concentrated under reduced pressure to give a yellow-brown oil (17 g). The crude product was crystallized from hexane/ethyl acetate 4:1 (5 ml/g) to give the title compound as a yellow solid, (13.09 g, 62.8%; 98.64% pure by GC normalization). Rf. 0.31 (silica, hexane/ethyl acetate, 3:1). $^1$H-NMR (300 MHz, CDCl$_3$) =1.35 (s, 9H), 2.48 (s, 3H), 4.12 (s, 2H), 5.91 (s, 1H), 6.47 (s, 1H), 7.34 (d, 2H), 7.75 (d, 2H) ppm. $^{13}$C-NMR (75 MHz, CDCl$_3$): 21.67, 27.81, 57.54, 81.73, 128.91, 129.70, 130.55, 132.53, 135.63, 144.83, 163.80 ppm. Analysis %: Found: C, 60.76; H, 6.80; C$_{15}$H$_{20}$O$_4$S requires: C, 60.79; H, 6.80.

b. tert-Butyl 2-(2-methoxyethoxymethyl)acrylate

To a suspension of the product of part (a) (14 g, 0.047 mmol) in 2-methoxyethanol (70 ml) at )° C. was added, in one portion, potassium carbonate (13.06 g, 0.094 mol) and the mixture stirred at 0° C. for 3 hours. The reaction was diluted with distilled water (100 ml) and extracted with dichloromethane (100 ml). The layers were separated and the aqueous layer further extracted with dichloromethane (50 ml) and the combined organic extracts concentrated under reduced pressure. The residue was purified by chromatography on silica eluting with hexane/ethyl acetate (6:1) to give, after combination and evaporation of appropriate fractions, the title compound as a colorless oil, (8.62 g, 84%). Rf. 0.32 (silica, hexane/ethyl acetate, 2:1. $^1$H-NMR (300 MHz, CDCl$_3$): 1.50 (s, 9H), 3.42 (s, 3H), 3.56-3.63 (m, 2H), 3.65-3.74 (m, 2H), 4.25 (s, 2H), 5.84 (s, 1H), 6.25 (s, 1H) ppm.

PREPARATION 8

2-Acetyl-2-[2-(4-nitrobenzyloxycarbonyl)ethyl]cyclohexanone

The title compound was prepared in 69% yield after chromatography (silica gel, gradient elution with hexane/ethyl acetate) from 2-acetylcyclohexanone and p-nitrobenzyl acrylate using a similar method to that used in Preparation 2. Rf. 0.2 (silica, hexane/ethyl acetate, 2:1). $^1$H-NMR (300 MHz, CDCl$_3$) 1.40-1.78 (m, 4H), 1.89-2.47 (m, 8H), 2.07 (s, 3H), 5.13 (s, 2H), 7.45 (d, 2H), 8.17 (d, 2H) ppm. Analysis %: Found: C, 62.75; H, 5.90; N, 3.87; C$_{18}$H$_{21}$NO$_6$ requires C, 62.24; H, 6.09; N, 4.03.

PREPARATION 9

2-Benzoyl-2-[2-(4-methoxybenzyloxycarbonyl)ethyl]cyclohexanone

The title compound was prepared in 65.5% yield after chromatography (silica gel, hexane/ethyl acetate 4:1) from 2-benzoylcyclohexanone and p-methoxybenzyl acrylate using a similar method to that used in Preparation 2. (M$^+$394.13, 53%). Rf. 0.39 (silica, hexane/ethyl acetate (2:1). $^1$H-NMR (300 MHz, CDCl$_3$): =1.38-1.49 (m, 1 H), 1.68-1.82 (m, 3H), 1.98-2.57 (m, 7H), 2.82-2.91 (m, 1H), 3.82 (s, 3H), 5.03 (s, 2H), 6.87 (d, 2H), 7.26 (d, 2H), 7.42 (t, 2H), 7.56 (t, 1H), 7.88 (d, 2H) ppm. Analysis %: Found: C, 73.05; H, 6.74; C$_{24}$H$_{26}$O$_5$ requires C, 73.08; H, 6.64.

PREPARATION 10

2-[2-(tert-Butoxycarbonyl)ethyl]-2-ethoxycarbonylcyclohexanone

To a solution of 2-ethoxycarbonylcyclohexanone (5.0 g, 0.029 mol) and tert-butyl acrylate (4.83 g, 0.037 mol) in tert-butanol (30 ml) was added, in one portion, potassium carbonate (4.0 g, 0.029 mol). The suspension was stirred at room temperature for 22 hours, diluted with dichloromethane (100 ml) and distilled water (100 ml) and the layers separated. The aqueous layer was extracted with dichloromethane (2×100 ml) and the combined dichloromethane extracts dried over magnesium sulphate, filtered and concentrated under reduced pressure. The residue was purified by chromatography on silica by eluting with hexane/ethyl acetate (4:1) to give, after combination and evaporation of appropriate fractions, the title compound as a colorless oil, (7.99 g, 92.3%; 98.92% by GC normalization) (MH$^+$299.03, 8.53%). Rf. 0.15 (silica, hexane/ethyl acetate 4:1). $^1$H-NMR (300 MHz, CDCl$_3$) =1.20 (t, 3H), 1.37 (s, 9H), 1.52-2.46 (m, 12H), 4.08-4.21 (m, 2H) ppm. $^{13}$C-NMR (62 MHz, CDCl$_3$) =13.97, 22.38, 27.36, 27.91, 29.52, 30.49, 36.06, 40.85, 59.87, 61.19, 80.10, 171.61, 172.22, 207.39 ppm. Analysis %: Found: C, 64.19; H, 8.80; C$_{16}$H$_{26}$O$_5$ requires C, 64.41; H, 8.78.

PREPARATION 11

2-Acetyl-2-[2-(tert-butoxycarbonyl)-3-(2-methoxyethoxy)propyl]cyclohexanone

To a suspension of 2-acetylcyclohexanone (3.5 g, 0.025 mol) and tert-butyl 2-(2-methoxyethoxymethyl)acrylate (see Preparations 6 and 7) (5.41 g, 0.025 mol) in acetonitrile (20 ml) was added, in one portion, potassium tert-butoxide (0.14 g, 0.0012 mol) at −10° C. The mixture was stirred at −10° C. for 24 hours, at 0° C. for 6 hours and at room temperature for 18 hours. The mixture was partitioned between ethyl acetate (15 ml) and distilled water (30 ml) and the layers separated. The aqueous layer was extracted with eithyl acetate (2×15 ml) and the combined ethyl acetate extracts concentrated under reduced pressure to give a brown oil (7.52 g). The residue was purified by chromatography on silica by eluting with hexane/ethyl acetate (4:1) to give, after combination and evaporation of appropriate fractions, the title compound as a colorless oil, (4.98 g, 55.8%). Rf. 0.23 (silica, hexane/ethyl acetate, 2:1). Analysis %: Found: C, 64.44; H, 9.02; $C_{19}H_{32}O_6$ requires: C, 64.02; H, 9.05.

I claim:

1. A process for preparing a compound of the formula:

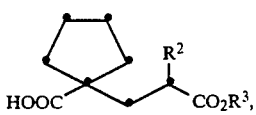

or a base salt thereof, wherein $R^2$ is hydrogen or $C_1$-$C_6$ alkyl optionally substituted by up to 3 substituents each independently selected from the group consisting of $C_1$-$C_6$ alkoxy and $C_1$-$C_6$ alkoxy ($C_1$-$C_6$ alkoxy)-; and $R^3$ is $C_1$-$C_6$ alkyl or benzyl, said benzyl group being optionally ring-substituted by up to 2 nitro or $C_1$-$C_4$ alkoxy substituents, comprising: reacting a compound of the formula:

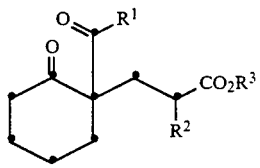

wherein $R^1$ is $C_1$-$C_4$ alkyl, phenyl, benzyl or $C_1$-$C_4$ alkoxy; and $R^2$ and $R^3$ are as previously defined for a compound of the formula (I), with peroxide ions.

2. The process of claim 1, further including conversion of the compound of formula (I) to a base salt thereof.

3. The process of claim 1 in which the source of the peroxide ions is hydrogen peroxide, a peroxy($C_1$-$C_4$) alkanoic acid, sodium perborate or a hydrate thereof, or sodium percarbonate, and in which water is present in said reacting step.

4. The process of claim 1 in which the source of the peroxide ions is hydrogen peroxide and in which water is present in said reacting step.

5. The process of claim 1 wherein said reacting step is carried out in a suitable solvent and in the presence of an acid.

6. The process of claim 1 wherein said reacting step is carried out in a suitable solvent and in the presence of a base.

7. The process of claim 5 wherein the solvent is tert-butanol.

8. The process of claim 5 wherein the acid is a mineral acid.

9. The process of claim 8 wherein the mineral acid is sulphuric acid.

10. The process of claim 1 wherein said reacting step is carried out in acetic acid.

11. The process of claim 6 wherein the base is selected from the group consisting of sodium hydroxide, sodium carbonate, sodium bicarbonate, potassium hydroxide, potassium carbonate, and potassium bicarbonate.

12. The process of claim 11 wherein the base is selected from the group consisting of sodium bicarbonate and potassium bicarbonate.

13. The process of claim 1 wherein $R^1$ is $C_1$-$C_4$ alkyl, phenyl or $C_1$-$C_4$ alkoxy; $R^2$ is hydrogen or $C_1$-$C_6$ alkyl optionally substituted by one $C_1$-$C_6$ alkoxy or $C_1$-$C_6$ alkoxy ($C_1$-$C_6$ alkoxy)- substituent; and $R^3$ is $C_1$-$C_6$ alkyl or benzyl, said benzyl group being optionally ring-substituted by one nitro or $C_1$-$C_4$ alkoxy substituted.

14. The of claim 13 wherein $R^1$ is methyl, phenyl or oxy; $R^2$ is hydrogen, 2-methoxyethoxymethyl, 2-methoxyethyl or methoxymethyl; and $R^3$ is ethyl, tert-butyl, benzyl, 4-nitrobenzyl or 4-methoxybenzyl.

15. The process of claim 13 wherein $R^1$ is methyl or ethoxy; $R^2$ is hydrogen or 2-methoxyethoxymethyl; and $R^3$ is tert-butyl.

16. A process for preparing a compound of the formula:

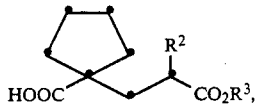

wherein $R^2$ is hydrogen or $C_1$-$C_6$ alkyl optionally substituted by up to 3 substituents each independently selected from the group consisting of $C_1$-$C_6$ alkoxy and $C_1$-$C_6$ alkoxy($C_1$-$C_6$ alkoxy)-; and $R^3$ is $C_1$-$C_6$ alkyl or benzyl, said benzyl group being optionally ring-substituted by up to 2 nitro or $C_1$-$C_4$ alkoxy substituents, comprising: reacting a compound of the formula:

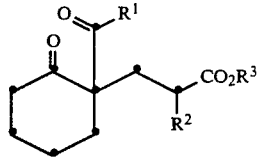

wherein $R^1$ is $C_1$-$C_4$ alkyl, phenyl or benzyl; and $R^2$ and $R^3$ are as defined for the formula (I), with a source of peroxide ions under acidic conditions.

* * * * *